(12) United States Patent
Gibson et al.

(10) Patent No.: US 6,368,867 B1
(45) Date of Patent: *Apr. 9, 2002

(54) MONITOR FOR VERIFICATION OF OZONE REACTION

(75) Inventors: Margaret Lecko Gibson, Underhill Center; John James Lajza, Jr., Essex Junction; Harold George Linde, Richmond, all of VT (US)

(73) Assignee: International Business Machines Corporation, Armonk, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,721

(22) Filed: Jan. 29, 1998

(51) Int. Cl.⁷ ................. G01N 33/00; G01N 31/22; G01N 21/01; G01N 21/25

(52) U.S. Cl. .......... 436/135; 436/2; 436/127; 436/166; 436/171; 422/62; 422/82.05; 422/82.09; 422/83; 422/86; 422/87

(58) Field of Search ............ 422/55–62, 82.05, 422/82.09, 83, 86, 87; 436/6, 127, 135, 166, 171, 174, 181, 1, 2

(56) References Cited

U.S. PATENT DOCUMENTS

| | | | |
|---|---|---|---|
| 1,368,346 A | | 2/1921 | Moisant |
| 3,305,852 A | * | 2/1967 | Cates, Jr. |
| 3,397,966 A | * | 8/1968 | Plantz ................. 436/135 |
| 3,859,045 A | * | 1/1975 | Lofquist et al. |
| 3,881,869 A | * | 5/1975 | Neti et al. ............ 436/135 |
| 3,975,159 A | * | 8/1976 | van Heusden ........ 436/135 |
| 4,381,922 A | * | 5/1983 | Frey et al. ............. 422/98 |
| 4,562,047 A | * | 12/1985 | Segtak et al. .......... 422/300 |
| 4,710,476 A | | 12/1987 | Ellis et al. |
| 4,859,607 A | * | 8/1989 | Lambert et al. ........ 436/135 |
| 5,052,382 A | | 10/1991 | Wainwright |
| 5,185,129 A | | 2/1993 | Koutrakis et al. |
| 5,415,838 A | | 5/1995 | Rieger et al. |
| 5,643,536 A | | 7/1997 | Schmelz |
| 5,668,301 A | | 9/1997 | Hunter |
| 5,788,925 A | * | 8/1998 | Pai et al. ................. 422/3 |
| 5,866,798 A | * | 2/1999 | Schönfeld et al. ...... 73/24.06 |
| 5,872,004 A | * | 2/1999 | Bolsen ................ 435/287.4 |
| 5,942,438 A | * | 8/1999 | Antonoplos et al. ...... 436/1 |

FOREIGN PATENT DOCUMENTS

| | | | |
|---|---|---|---|
| CA | 2141265 | * | 7/1995 |
| EP | 419282 | * | 3/1991 |
| WO | 9614573 | * | 5/1996 |

OTHER PUBLICATIONS

H. Tomiyasu et al, Anal. Chem. 56, 752–754, Apr. 1984.*
T. V. Fomina Zashch. Met. 20, 790–792, May 1984.*
T. Fukusima et al, Proc.—Electrochem. Soc. 1992, 93–1, 221–234.*

(List continued on next page.)

Primary Examiner—Arlen Soderquist
(74) Attorney, Agent, or Firm—Scully, Scott, Murphy & Presser; James M. Leas

(57) ABSTRACT

The present invention provides an ozone processing monitor and a method of using the same in ozone processing to determine whether sufficient ozone treatment has occurred on a production part needing ozone treatment. The ozone processing monitor of the present invention comprises an ozone sensitive material which is capable of thinning, bleaching, forming an oxide layer or undergoing any other physical or chemical change upon exposure to ozone, wherein said physical or chemical change produces a visible color change of said ozone sensitive material which can be monitored during or following ozone processing. The color change of the ozone sensitive material can be compared to standards to determine if too little, too much or appropriate ozone treatment has occurred.

24 Claims, 4 Drawing Sheets

OTHER PUBLICATIONS

B. Stockle et al, *Werkst. Korros.* 44, 48–56, Feb. 1993.*
T. Gotoh *Atmos. Environ.* 27A, 565–571, Apr. 1993.*
A. Ronnquist *Chem. Abstr*, 1969, 71, 104559w.*
V.S. Salvin *Text. Chem. Color.* 1969, 1, 332–334.*
N. Azzerri et al. *Corrosion* 1970, 26, 381–386.*
G. Trabanelli et al. *Chem. Abstr*, 1974, 80, 21982p.*
R.J. Rubin Report, 1980, NBSIR–80–1975.*
K.Sawatari *Ind. Health* 1984, 22, 117–126.*
M.R. Surgi et al, *Anal. Chem*, 1985, 57, 1737–1740.*
H.M. Fog et al, *Anal. Chem*, 1985, 57, 2634–2638.*
R.D. Van Valin et al. *Proc.—Annu, Conf., Am. Water Works Assoc.* 1989, 1293–1299.*
D. Grosjean et al. *Atmos. Environ., Part A* 1992, 26A, 1407–1411.*
T. Iikawa et al, *Corros. Sci.* 1993, 35, 735–742.*
H. Guesten et al. *Chem. Abstr.* 1994, 120, 171783h.*
J. Garcia–Anton et al. *Corrosion* 1995, 51, 558–566.*
M. Hangartner et al. *Analyst* 1996, 121, 1269–1272.*

* cited by examiner

MONITOR FOR VERIFICATION OF OZONE REACTION

FIELD OF THE INVENTION

The present invention relates to ozone processing and, in particular, to an ozone processing monitor which can be used in ozone processing to determine whether sufficient ozone treatment has occurred on a production part needing ozone treatment. Specifically, the ozone processing monitor of the present invention comprises an ozone sensitive material which is capable of producing a visual color change upon exposure to ozone. In one embodiment, the ozone sensitive material employed in the present invention is capable of forming a surface oxide layer upon exposure to ozone that produces a visible color change in the ozone sensitive material which can be used in determining if too little, too much or appropriate ozone treatment is occurring. In another embodiment of the present invention, the ozone sensitive material is an organic material that oxidizes and consequently thins during ozone treatment. In yet another embodiment, the ozone sensitive material is a chromophoric compound such as a dye that bleaches during exposure to ozone.

The ozone processing monitor of the present invention represents an advancement over prior art ozone processing monitors since it is evaluated during or following the actual ozone processing, i.e. real time basis, not several processing steps later as is required by prior art ozone monitors. The present invention also provides a method of using the inventive ozone processing monitor during or following ozone processing to determine whether sufficient ozone treatment has occurred. The monitor of the present invention can also be used to determine chamber uniformity, chamber to chamber variations, or process variables such as time, pressure, temperature or concentration.

PRIOR ART

In semiconductor lead-on-chip (LOC) memory packaging, ozone is used to alter the surface of the polymeric adhesive of the die attach tape in a manner which enhances adhesion between the polymeric adhesive and the mold compound. A major problem in this area has been the lack of an ozone processing monitor that indicates the health of the ozone process on a real time basis. Traditionally, acoustical scanning of the molded product is performed several process steps after ozone treatment to determine effectiveness of the ozonation as evidenced by delamination within the final package.

This prior art technique suffers because the process time between ozone and the molding operation allows a significant amount of the product to be built defective. That is, products exhibiting delamination can pass final testing but fail at a later date; therefore product lots exhibiting delamination must be discarded or 100% acoustically scanned to identify and remove the defective parts.

Moreover, post ozone delamination has been found to be caused by either adhesive failure at the mold compound/tape adhesive interface or cohesive failure within the tape adhesive. It has been determined that adhesive failure results from insufficient ozone treatment, whereas cohesive failure is caused by excessive ozonation. The failure mode of the delamination must be determined by a time consuming cross sectional technique resulting in extensive down time of the ozone operation while the failure mechanism is determined.

Although the prior art discloses many different types of flow-through ozone monitors such as described, for example, in U.S. Pat. Nos. 5,185,129 to Koutrakis, et al. and 5,052,382 to Wainwright, there still exists a need for developing a new and improved ozone monitor which is not an ozone concentration monitor but an ozone reaction monitor for a process. That is, there is a need for providing an ozone monitor which provides information regarding the ozone process effectiveness on a real time basis, not several processing steps after the product is formed, as is required in typical prior art ozone processing. Moreover, there is a need for providing an ozone processing monitor which can differentiate between too little and excessive ozone treatment such that, if either is detected, the malfunctioning ozone chamber or process can be stopped and the processing reaction conditions readjusted or chamber repaired so as to provide effective ozone treatment to a production part.

SUMMARY OF THE INVENTION

One object of the present invention is to provide an ozone processing monitor which can be employed on a real time basis to monitor whether sufficient ozone treatment has occurred on a production part needing such treatment.

Another object of the present invention is to provide an ozone processing monitor which is easy to use and which can readily differentiate between too little, too much or appropriate ozone treatment.

A further object of the present invention relates to an ozone processing monitor which provides a visible change in the monitor material that correlates to the ozone reaction on the production part and thus can be used to initiate and regulate changes in the ozone processing conditions.

A yet further object of the present invention is to provide an ozone processing monitor which adds no significant cost to the operation and which can be used without contaminating the production part being processed.

These as well as other objects and advantages are achieved in the present invention by utilizing an ozone processing monitor comprising an ozone sensitive material which is capable of undergoing a physical or chemical change upon exposure to ozone, wherein said physical or chemical change produces a visible color change of said ozone sensitive material which can be monitored during, or evaluated after, ozone processing.

The term "physical or chemical change" is used herein to denote that upon exposure to ozone the appearance of the ozone sensitive material is sufficiently altered so as to provide a visible color change in the material. This can be obtained in the present invention, for example, by thinning, bleaching or forming an oxide layer in the ozone sensitive material. Since the color change is directly proportional to the reaction of ozone, the monitor of the present invention is a viable means for determining if too much, too little or appropriate ozone treatment has occurred within the chamber or on a production part needing ozone treatment.

As stated above, the ozone sensitive material employed in the present invention is a material which is capable of undergoing a physical or chemical change, e.g. forming an oxide layer, thinning or bleaching, upon exposure to ozone. Any of the foregoing produces a visible color change in the ozone sensitive material that can be used in the present invention as a reaction monitor for ozone processing.

Another aspect of the present invention relates to a method of using the above described ozone processing monitor to determine whether sufficient ozone treatment has occurred on a production part. In accordance with this aspect of the present invention, the method comprises the steps of:
(a) providing a production part requiring ozone treatment and an ozone sensitive material which is capable of undergoing a physical or chemical change upon exposure to ozone into an ozone processing reactor chamber, wherein said physical or chemical change produces a color change of said ozone sensitive material which can be monitored during or following ozone processing;

(b) introducing ozone into said reactor chamber; and (c) monitoring the color change of the ozone sensitive material and comparing the same to standards of the same ozone sensitive material, wherein said standards have been previously treated with ozone under various reaction conditions so as to provide a spectrum of colors which can be employed to determine whether sufficient ozone treatment has occurred on said production part.

In accordance with the method of the present invention, the ozone treatment may be stopped at any time during the operation if the color of the ozone processing monitor is below a minimum threshold or above a maximum threshold. This can be easily done in the method of the present invention by comparing the ozone processing monitor to the standards having a spectrum of color associated therewith which corresponds to various levels of ozone treatment.

The present invention also provides a method of monitoring the uniformity and effectiveness of an ozone reactor system. In accordance with this aspect of the present invention, an ozone sensitive material as described hereinabove is introduced into an ozone reactor chamber, exposed to ozone and thereafter evaluated by comparing the exposed ozone sensitive material to standards that were previously reacted with ozone over a range of process parameters such as time, pressure, temperature and ozone concentration.

DETAILED DESCRIPTION OF THE INVENTION

Figure 1:
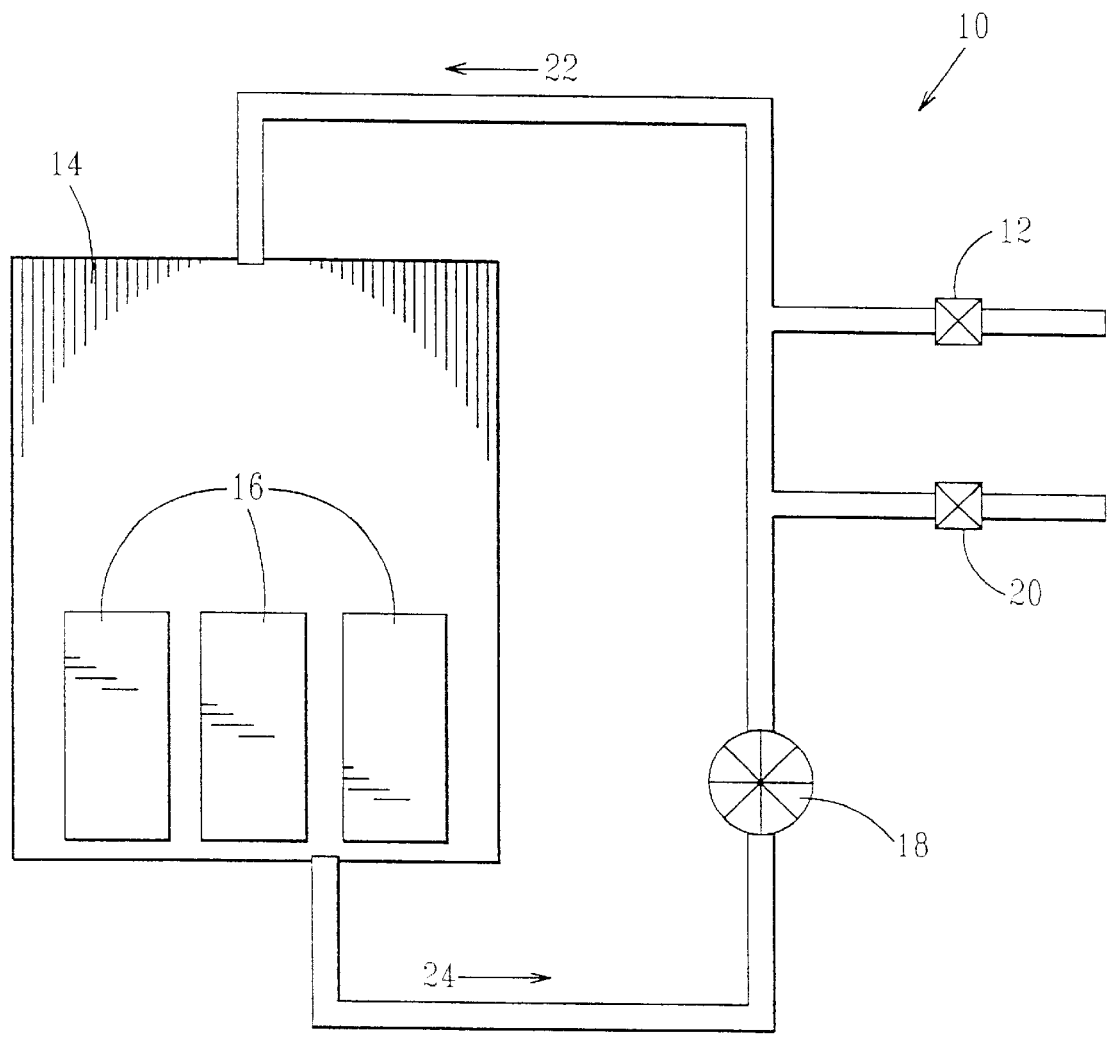
FIG. 1 is a diagram of an ozone reaction chamber that can be employed in the present invention.

As stated above, the present invention provides an ozone processing monitor which is capable of providing real time information to its user prior to or following treatment of a desired product, i.e. production part. The ozone processing monitor of the present invention comprises an ozone sensitive material which is capable of forming a color change upon exposure to ozone which can be monitored and compared to standards of like ozone sensitive material which have been previously treated with ozone so as to provide a spectrum of color which is directly dependent on the reaction of ozone.

Any material that is ozone sensitive can be employed in the present invention as the ozone processing monitor as long as the material provides visible discrimination of ozone processing results, i.e. color changes caused by surface oxide growth, thinning, bleaching or any other physical or chemical change of said material. Suitable ozone sensitive materials include, but are not limited to: metallic materials, organic materials, polymeric materials, dyed materials, organometallic materials and the like.

Examples of metallic materials that can be employed in the present invention as the ozone sensitive material include metals selected from the group consisting of Cu, Zn, Sn, Fe, Ti, V, Ni, Ag and mixtures or alloys thereof, e.g. brass or bronze. A highly preferred metallic ozone sensitive material that is employed in the present invention is brass.

Illustrative examples of polymeric materials that may be employed in the present invention include, but are not limited to: polyimides, polystyrenes, phenolic resins, poly (alkylenes) and acrylates. Typically, the polymeric material is in the form of a polymer film which thins when it is exposed to ozone.

Examples of dyed materials that can be employed in the present invention as the ozone sensitive material are diazo dyes and coumarin dyes, whereas siloxanes and porphyrins are illustrative examples of typically organometallic materials that can be employed in the present invention.

The ozone sensitive material employed in the present invention may comprise any shape or size depending upon only the size of the ozone reactor chamber employed. Thus, the size and shape of the ozone sensitive material is not critical to the instant invention. For a commonly employed ozone reactor chamber, the ozone sensitive material is in the form of a thin strip, process article, slug, fabric or film.

The ozone sensitive material can be processed into the desired shape and size utilizing any conventional technique well known to those skilled in the art. If necessary, the ozone sensitive material employed in the present invention can be treated, i.e. cleaned, prior to use to remove any materials such as surface contaminants that may adversely affect the color change generated during ozone processing. Any technique that is capable of removing such materials from the ozone sensitive material may be employed in the present invention. Examples of such removal techniques include, but are not limited to: the use of an organic solvent and/or an acid, polishing, or chemical-mechanical polishing (CMP).

The present invention also contemplates employing combinations of these removal techniques.

Typical organic solvents that can be employed in the removal of the surface material include, but are not limited to: degreasers such as freons, chlorinated hydrocarbons, and aliphatic and aromatic hydrocarbons; thinners such as lacquer thinner, acetone, ketones, esters and ethers; cleaning solvents such as N-methyl pyrrolidone (NMP), dimethyl-sulfoxide (DMSO), surfactants, detergents or combinations or mixtures thereof; whereas, HCl, HF, $HNO_3$, $H_2SO_4$ and mixtures thereof are examples of suitable acids that may be employed.

The organic solvents and/or acids may be employed by immersing the ozone sensitive material in a bath containing the same or by applying the organic solvent and/or acid to the ozone sensitive material by spraying, brushing and the like. The exact conditions employed in removing the surface contaminants from the ozone sensitive material varies depending on the type of ozone sensitive material being employed and the surface contaminants.

If the ozone sensitive material is to be stored prior to use, it should be sealed in a suitable material or container which prevents the same from being exposed to air, moisture or another ozone-containing ambient. This includes the use of a suitable wrapper such as a polyolefin that prevents tarnishing or oxidation of the ozone sensitive material of the present invention.

The above provides a description of the ozone sensitive material that is employed in the present invention as the ozone processing monitor. The following description provides an illustration on how the same is employed to monitor the ozone process.

As stated above, the ozone sensitive material and a production part to be subjected to ozone processing are introduced into a reactor chamber which is at least capable of introducing ozone therein. Any reactor chamber can be employed in the present invention so long as ozone can be introduced therein. A typical ozone reactor that can be employed in the present is illustrated in FIG. 1. Specifically, the ozone reactor 10 shown in FIG. 1 includes ozone inlet 12, chamber 14, production load 16, circulation fan 18 and vacuum outlet 20. The introduced ozone flows in the direction indicated by arrows 22 and 24.

The above-mentioned items, i.e. ozone sensitive material and production part, may be introduced to the reactor chamber by hand or by machinery. No matter which technique is employed, care should be taken so as not to overexpose the ozone sensitive material to air or another ozone-containing ambient prior to use.

The types of production parts to be subjected to ozone processing are not limited in the present invention. Thus, any production part that needs to be treated with ozone can be employed in the present invention. One area where the present invention is highly applicable is lead-on-chip (LOC) memory packaging. Thus, the production part in such LOC applications would include a die attach tape that has one of its surfaces bonded to a lead frame and the other surface bonded to a semiconductor chip surface which may contain a plurality of bond pads thereon for wire bonding to the lead frame. Ozonation of the exposed adhesive is required.

According to the next step of the present invention, ozone is introduced into the reactor chamber utilizing conditions that are suitable for processing the desired production part. Specifically, the processing conditions may vary depending on the desired product being produced; the only limitation being that there is sufficient ozone to ozonate the production part being fabricated. In LOC applications, ozone is generally introduced into the reactor chamber at a concentration of from about 1 to about 1000 ppm, a pressure of from about 100 to about 1200 mbar, for a time period of from about 1 to about 1000 minutes and at a temperature of from about −40° to about 300° C. More preferably, in LOC applications, ozone is introduced at a concentration of from about 100 to about 250 ppm, a pressure of from about 700 to about 1000 mbar, for a time period of from about 5 to about 150 minutes and at a temperature of from about 150 to about 25° C. As stated above, the concentration, pressure, reaction time and temperature may vary significantly from the values indicated above depending upon the desired production part being fabricated. The exact processing conditions are predetermined and are selected so as not to cause any defects in or to the final processed production part. In the present invention, ozone is typically introduced in combination with air.

The monitor of the present invention, i.e. ozone sensitive material, can be monitored either during or after ozone processing and the color change observed is compared to standards of the same ozone sensitive material which have been previously subjected to ozone processing using various reaction conditions that are effective in providing a full spectrum of color. Thus, the standards can be used as a monitor gauge to determine if too little, too much or appropriate ozone treatment is occurring.

In the present invention, the standards, i.e. monitor gauge, can be prepared at a given pressure by either (i) using different concentrations of ozone over a fixed time, (ii) using a fixed concentration of ozone over variable time periods, or (iii) fixing the ozone concentration and the time and varying the temperature. When used in LOC memory cell applications, it is preferred that the standards be processed at a fixed temperature and concentration of ozone, e.g. 200 ppm, at variable times, e.g. 0, 15, 30, 45 and 60 minutes, with production parts. The sample products are molded and acoustically scanned for delamination at the tape interface. The standards for each process variation are typically fastened to a backer for comparison with subsequent runs.

In the above LOC applications, delamination was found to occur on the 0 and 60 minute samples, therefore, an ozone process was defined at 30 minutes at 200 ppm with process shut down at colors lighter than the 15 minute gauge or darker than the 45 minute gauge.

In addition to being employed as described above, the ozone processing monitor of the present invention can be employed to qualify a new chamber or determine chamber uniformity. That is, the ozone processing monitor can be employed as a means for determining the actual level of ozonation achieved in areas of the reactor chamber under a variety of process conditions. When employed for such a purpose, the ozone processing monitor or plurality of monitors of the present invention are introduced into the chamber of the ozone reactor and positioned therein. Next, ozone is introduced into the reactor chamber containing said ozone processing monitors and thereafter the exposed ozone processing monitors are evaluated by comparing the same to standards which have been previously reacted with ozone over a range of process parameters such as time, pressure, temperature and concentration.

The following examples are given to illustrate the scope and spirit of the present invention. Because these examples are given for illustrative purposes only, the invention embodied therein should not be limited thereto.

EXAMPLE 1

Figure 2:
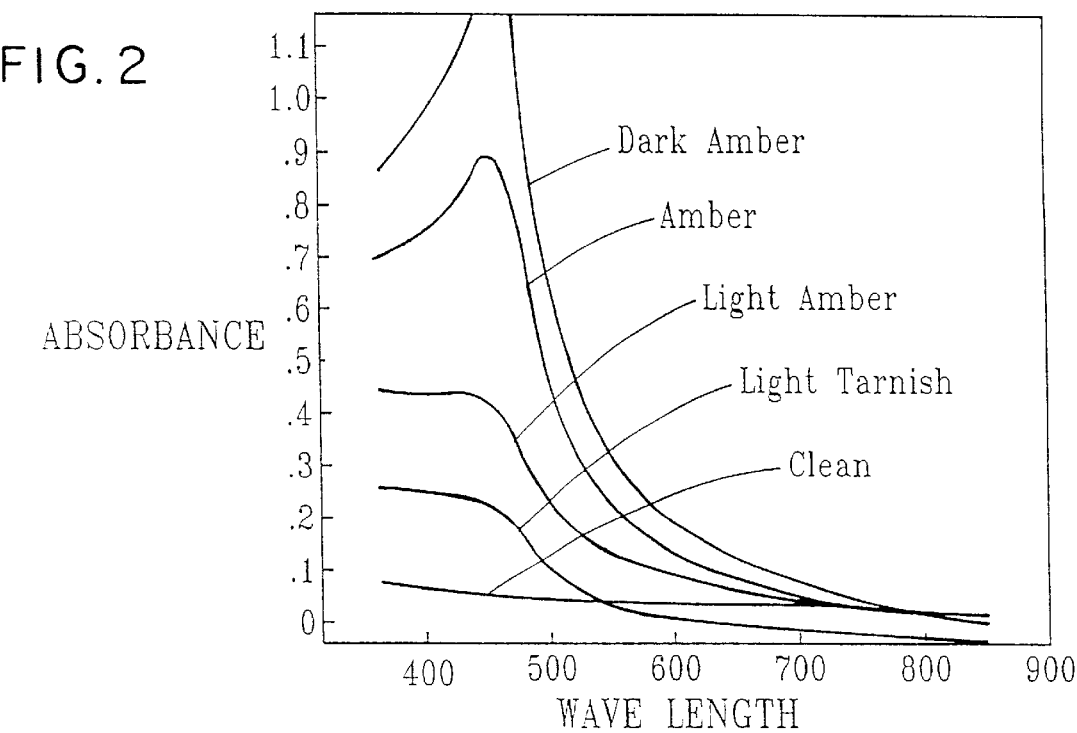
FIG. 2 is a plot of Absorbance vs. Wavelength (nm) of various brass strips as treated in Example 1.
Figure 3:
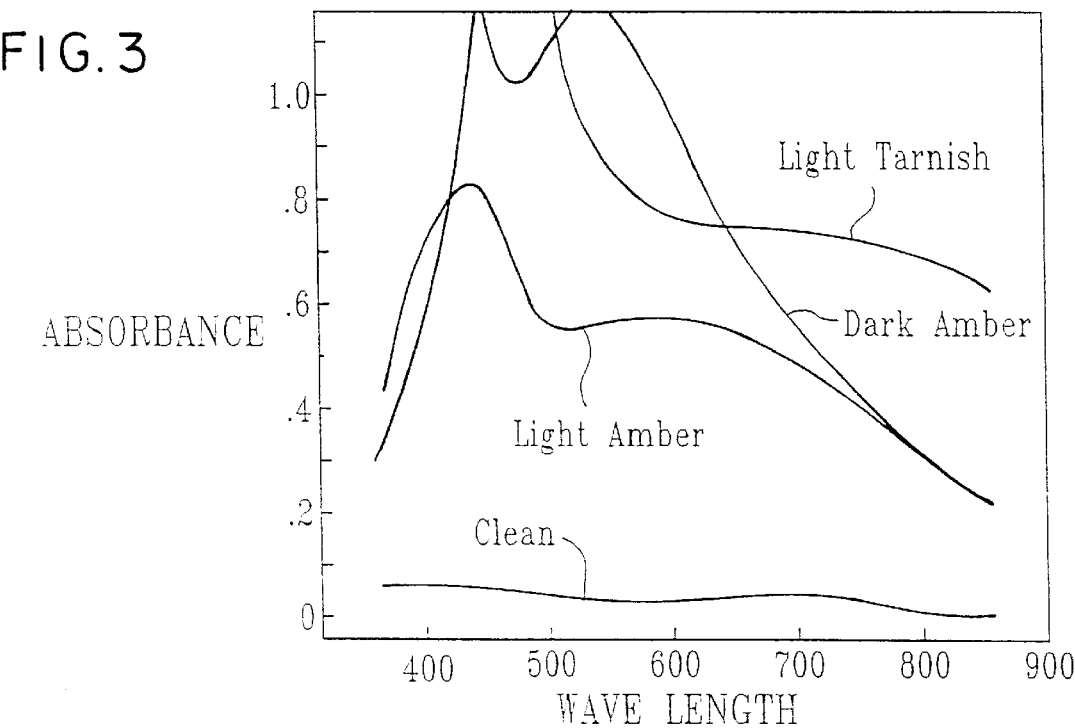
FIG. 3 is a plot of Absorbance vs. Wavelength (nm) of various brass strips as treated in Example 1.
Figure 4A:
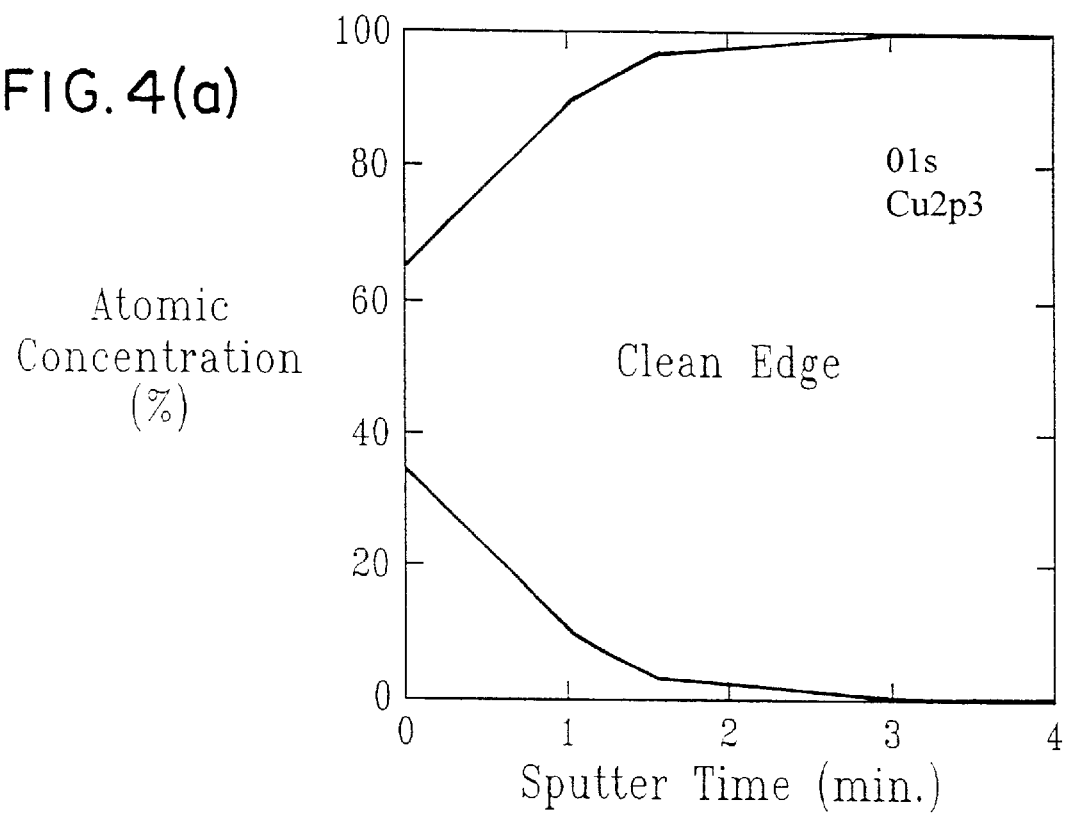
FIGS. 4(a)–(d) are ESCA sputter depth profiles of (a) clean Cu film, (b) antique Cu film, (c) magenta Cu film, and (d) blue Cu film.
Figure 4B:
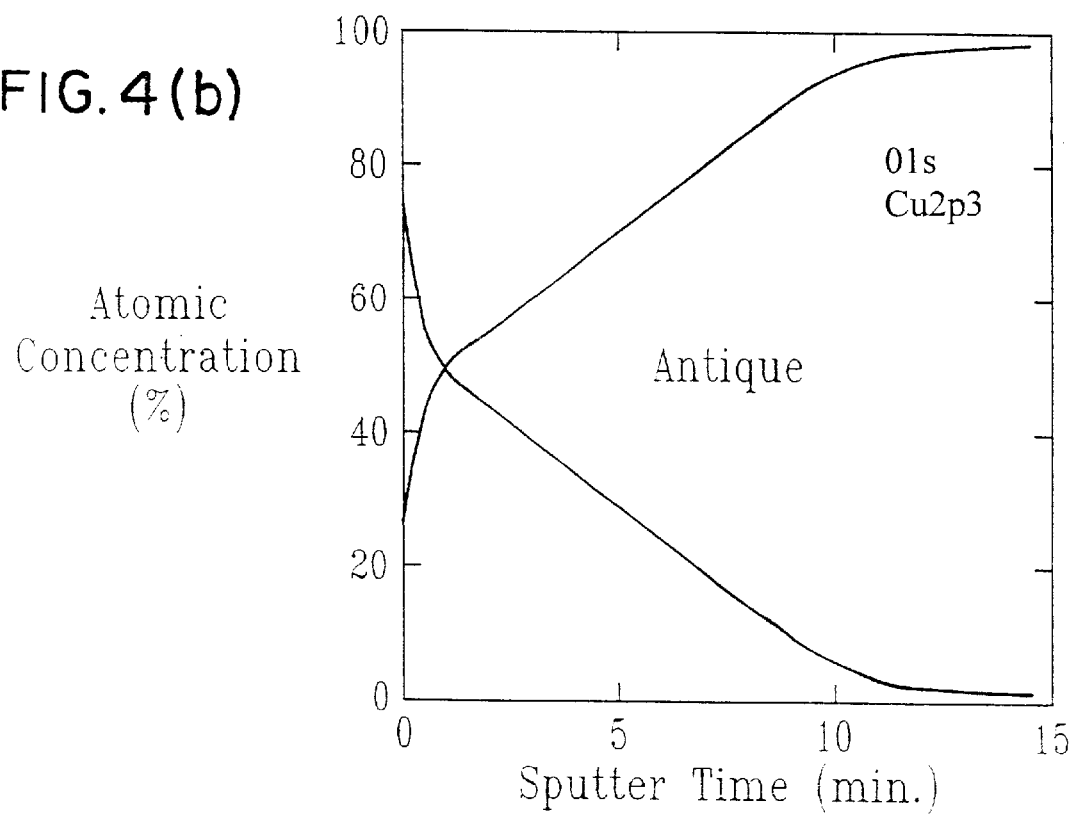
Figure 4C:
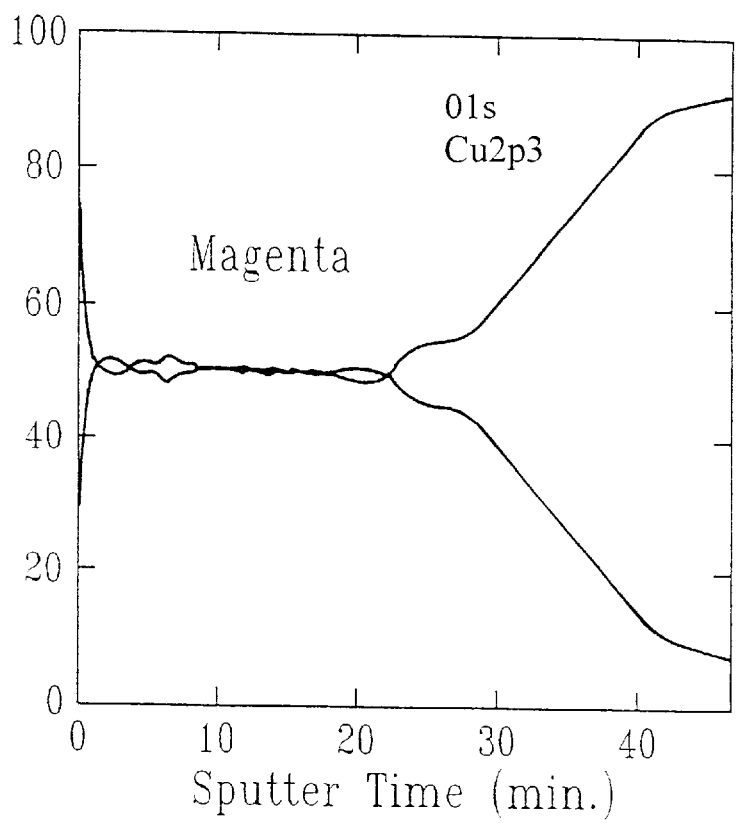
Figure 4D:
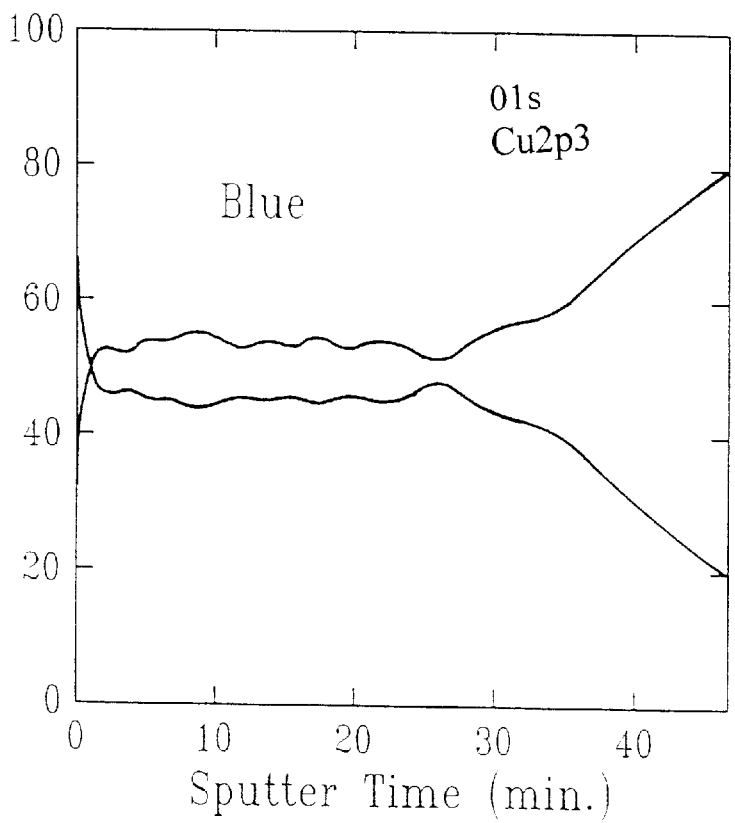

In this example, brass (70% Cu and 30% Zn) was employed as the ozone sensitive material. Specifically, samples of clean brass strips (8 mil thick, 40±1 mm wide by 249.5±3 mm long) were subjected to an ozone ambient of 200 ppm ozone in air at about 800 mbar for 52 min. in a processing lead frame rack capable of holding horizontal strips or lead frames. These sample strips exhibited color variations on the lead edge but attained a highly visible greenish brown coloration over the remaining area. As a result of good film visibility, additional brass strips were subjected to the same ozone treatment as mentioned above for times of 5, 15, 30, 45 and 60 minutes. Such treatment produced film colors from light amber to a dark green amber mix. A sample from each process variation was then scanned by UV reflection to determine the corresponding absorption curve. These scans are shown in FIGS. 2 and 3, respectively. Product samples from each of these process variations were thereafter processed through molding and inspected for delamination with an acoustic microscope. Tables 1 and 2 show the combined results for the spectrophotometer scan and the acoustic scan. In FIG. 2, scans of the shades of amber follow a well behaved ascending order. The scans of the darker films, FIG. 3, produce two maxima, typical of thicker surface oxide films which are outside of the range desired for this particular application.

TABLE 1

| Sample # | Process Time (min) | Absobance at 400 nm | Absorbance at 700 nm | Color | Delamination |
|---|---|---|---|---|---|
| 3 | 5 | 0.163 | −0.041 | Slight tarnish | Yes |
| 2 | 15 | 0.341 | 0.009 | Light amber | No |
| 4 | 30 | 0.636 | 0.018 | Amber | No |
| 1 | 45 | 0.818 | 0.041 | Dark amber | No |

TABLE 2

| Sample # | Process Time (min) | Absorbance at 400 nm | Absorbance at 700 nm | Color | Delamination |
|---|---|---|---|---|---|
| 1A | 60 | 0.618 | 0.405 | Light green | Yes |
| 2A | >60 | Off scale | 0.477 | Brown | NA |
| 3A | >60 | 0.52 | 0.668 | Green | NA |

EXAMPLE 2

In this example, copper, Cu, was employed as the ozone sensitive material to monitor the ozone processing configuration and uniformity. Specifically, samples of clean Cu lead frames were prepared and processed in an ambient of air and 200 ppm ozone at about 800 mbar for 52 minutes. The processed samples exhibited discoloration at the surface. The color hues of the oxidized strip varied from clean copper where the strip was protected through pink copper (antique), magenta and blue on the leading edge of the strip. This variation revealed process nonuniformity possibly caused by turbulence. The gas was adjusted so that the turbulent area did not extend to the active region occupied by the first chip. The remaining portions of the strip were a uniform antique Cu color. Electron Spectroscopy for Chemical Analysis (ESCA) sputter depth profiles are shown in FIGS. 4(a)–(d) for the clean, antique, magenta and blue color regions, respectively. Surface oxide thickness for each of these regions relative to $SiO_2$ sputter rate are shown in Table 3 below. The different color regions were also subjected to Thin Film Analyzer (TFA) measurements. The surfaces of the samples were too rough to produce meaningful TFA data. No further experimentation was carried out using Cu strips.

TABLE 3

| Color | Copper | Antique | Magenta | Blue |
|---|---|---|---|---|
| Surface Oxide Thickness (Å) | 17 | 202 | 1066 | 1325 |

While the invention has been particularly shown and described with respect to preferred embodiments thereof, it will be understood by those skilled in the art that changes in form and detail may be made without departing from the spirit and scope of the instant invention.

What is claimed is:

1. A method for monitoring ozone treatment during or after ozone processing, comprising the steps of:
   (a) providing a production part requiring ozone treatment and an ozone sensitive material which is capable of undergoing a physical or chemical change upon exposure to ozone into an ozone processing reactor chamber, wherein said physical or chemical change produces a visible color change of said ozone sensitive material which can be monitored during or after ozone processing;
   (b) introducing ozone into said reactor chamber; and
   (c) monitoring the color change of said ozone sensitive material and comparing the same to ozone treated standards of said same ozone sensitive material, wherein said standards have been previously treated with ozone under various reactor conditions so as to provide a spectrum of colors which can be employed to determine whether said production part has been effectively treated with ozone.

2. The method of claim 1 wherein said production part comprises a die attach tape which has a lead frame bonded to one of its surfaces and a semiconductor chip bonded to its other surface.

3. The method of claim 1 wherein said ozone is introduced at a concentration of from about 1 to about 1000 ppm, a pressure of from about 100 to about 1200 mbar and for a time period of from about 1 to about 1200 minutes.

4. The method of claim 3 wherein said ozone is introduced at a concentration of from about 100 to about 250 ppm, a pressure of from about 700 to about 1000 mbar and for a time period of from about 5 to about 150 minutes.

5. The method of claim 1 wherein said ozone is introduced in combination with air.

6. The method of claim 1 wherein said ozone sensitive material is a metallic material, polymeric material, organic material, organometallic material or dyed material.

7. The method of claim 6 wherein said metallic material is selected from the group consisting of Cu, Zn, Fe, Ti, Sn, V, Ni, Ag and mixtures or alloys thereof.

8. The method of claim 7 wherein said metallic material is a brass alloy.

9. The method of claim 6 wherein said polymeric material is a polyimide, a polystyrene,-a poly(alkylene), a phenolic resin or an acrylate.

10. The method of claim 6 wherein said dyed material is a diazo dye or a coumarin dye.

11. The method of claim 6 wherein said organometallic is a siloxane or a porphorin.

12. A method of monitoring an ozone reactor system comprising:
   (i) introducing and positioning at least one substrate comprising an ozone sensitive material into an ozone reactor system, wherein said ozone sensitive material is a metallic material which is capable of undergoing a physical or chemical change upon exposure to ozone that measurably changes a thickness of said ozone sensitive material or a reaction product thereof;
   (ii) introducing ozone into said reactor system; and
   (iii) evaluating said thickness change of said ozone sensitive material or said reaction product on said at least one substrate by comparing the at least one ozone treated substrate to standards which have been previously reacted with ozone over a range of process parameters to determine the effectiveness of said ozone reactor system.

13. The method of claim 12 wherein said ozone is introduced at a concentration of from about 1 to about 1000 ppm, a pressure of from about 100 to about 1200 mbar and for a time period of from about 1 to about 1200 minutes.

14. The method of claim 13 wherein said ozone is introduced at a concentration of from about 100 to about 250 ppm, a pressure of from about 700 to about 1000 mbar and for a time period of from about 5 to about 150 minutes.

15. The method of claim 12 wherein said ozone is introduced in combination with air.

16. The method of claim 12 wherein said metallic material is selected from the group consisting of Cu, Zn, Fe, Ti, Sn, V, Ni, Ag and mixtures or alloys thereof.

17. The method of claim 16 wherein said metallic material is a brass alloy.

18. The method of claim 12 wherein a plurality of said at least one substrate is employed to determine uniformity of said ozone reactor system.

19. An apparatus comprising:
(a) a reactor chamber capable of receiving and maintaining ozone;
(b) a treatment zone in said reactor chamber wherein a production part requiring ozone treatment can be positioned; and
(c) an ozone process monitor comprising an ozone sensitive material which is capable of undergoing a physical or chemical change upon exposure to ozone that measurably changes a thickness of the ozone sensitive material or a reaction product thereof, wherein said ozone sensitive material is a metallic material which is used to determine whether said production part has been effectively treated with ozone by evaluating said thickness change of said ozone sensitive material or said reaction product by comparing the ozone treated production part to standards.

20. The apparatus of claim 19 wherein said metallic material is selected from the group consisting of Cu, Zn, Fe, Sn, Ti, V, Ni, Ag and mixtures or alloys thereof.

21. The apparatus of claim 20 wherein said metallic material is a brass alloy.

22. The apparatus of claim 17 wherein said ozone sensitive material is in the form of a trip, production article, slug, fabric or film.

23. The apparatus of claim 17 wherein said ozone sensitive material is treated prior to use to remove any surface materials which may adversely affect the formation of said physical or chemical change.

24. The apparatus of claim 19 wherein said ozone processing monitor comprises a brass alloy which is capable of forming an oxide layer upon exposure to ozone, wherein said oxide layer produces a visible color change of said brass alloy which can be monitored during or after ozone processing.

* * * * *